(12) United States Patent
Brottier et al.

(10) Patent No.: US 12,336,760 B2
(45) Date of Patent: Jun. 24, 2025

(54) METHOD FOR EVALUATING THE STABILITY OF A TEAR FILM

(71) Applicant: E-SWIN DEVELOPPEMENT, Houdan (FR)

(72) Inventors: Yves-Vincent Brottier, Adainville (FR); Arnaud Obin, Paray-Douaville (FR); Nelson Perrin, Sainte-Mesme (FR)

(73) Assignee: E-SWIN DEVELOPPEMENT, Houdan (FR)

( * ) Notice: Subject to any disclaimer, the term of this patent is extended or adjusted under 35 U.S.C. 154(b) by 516 days.

(21) Appl. No.: 17/753,696

(22) PCT Filed: Sep. 11, 2020

(86) PCT No.: PCT/FR2020/051579
§ 371 (c)(1),
(2) Date: Mar. 11, 2022

(87) PCT Pub. No.: WO2021/048510
PCT Pub. Date: Mar. 18, 2021

(65) Prior Publication Data
US 2022/0330814 A1 Oct. 20, 2022

(30) Foreign Application Priority Data
Sep. 13, 2019 (FR) .................................. 1910140

(51) Int. Cl.
*A61B 3/10* (2006.01)
(52) U.S. Cl.
CPC .................................. *A61B 3/101* (2013.01)
(58) Field of Classification Search
CPC ...................................................... A61B 3/101
(Continued)

(56) References Cited

U.S. PATENT DOCUMENTS

| 2010/0253907 A1 | 10/2010 | Korb et al. |
| 2015/0173610 A1 | 6/2015 | Munoz |
| 2015/0257639 A1 | 9/2015 | Manquez Hatta et al. |

FOREIGN PATENT DOCUMENTS

| JP | 2006204773 | 8/2006 |
| RU | 94046368 | 9/1996 |

(Continued)

OTHER PUBLICATIONS

International search report for PCT/FR2020/051579 dated Nov. 26, 2020.

*Primary Examiner* — Wyatt A Stoffa
*Assistant Examiner* — Grant A Gagnon
(74) *Attorney, Agent, or Firm* — Perman & Green, LLP

(57) ABSTRACT

Method for measuring the stability of a tear film of a patient using a device including a backlit translucent plate provided with a test chart positioned in front of at least one eye of the patient, at least one digital photographic camera connected to a computing system, and a camera lens pointing towards the patient's eye to photograph a reflection of a test chart pattern on the patient's. The method includes, from a starting time constituted by an eyelid blink, capturing a succession of images, detecting a succession of micro-movement areas in the images, and computing and storing data on the position, surface area and number of micro-movement areas of the tear film in each image, and computing and storing surface area and number of micro-movement areas of the tear film, and a measurement of the amplitude of the micro-movement areas as a function of time.

13 Claims, 17 Drawing Sheets

(58) Field of Classification Search
USPC .......................................................... 351/206
See application file for complete search history.

(56) References Cited

FOREIGN PATENT DOCUMENTS

| | | |
|---|---|---|
| RU | 2567829 | 11/2015 |
| RU | 2604942 | 12/2016 |
| RU | 2662273 | 7/2018 |
| WO | 2015073986 | 5/2015 |
| WO | 2016033590 | 3/2016 |
| WO | 2018156022 | 8/2018 |

METHOD FOR EVALUATING THE STABILITY OF A TEAR FILM

CROSS-REFERENCE TO RELATED APPLICATIONS

This application is a National Stage of International Application No. PCT/FR2020/051579, having an International Filing Date of 11 Sep. 2020, which designated the United States of America, and which International Application was published under PCT Article 21(2) as WO Publication No. 2021/048510 A1, which claims priority from and the benefit of French Patent Application No. 1910140, filed on 13 Sep. 2019, the disclosures of which are incorporated herein by reference in their entireties.

BACKGROUND

Field

The present disclosure relates to the field of detection of dry eye syndrome.

Brief Description of Related Developments

Tests for evaluating dry eye syndrome conventionally employ a test involving fluorescence. The practitioner instills a drop of fluorescein into the patient's eye and fluorescence is observed using a slit lamp. The practitioner determines the time between the blink of an eyelid and the appearance of the first non-fluorescent region. This time is the measurement of the "break-up time" or TBUT of the tear film. This method results in a measurement of a first break-up time, whether the break-up is due to a local defect such as a speck of dust or a real dry-eye problem. The times measured are of the order of 6 to 10 seconds.

Other evaluating methods, which measure what is called "non-invasive break-up time" or NIBUT, are non-invasive methods for measuring break-up time. Tests employing such methods especially use reflection from the cornea of a test chart provided with a pattern made up of concentric circles and of radial lines.

When the film breaks up, the lines and/or circles of the reflected pattern become deformed or regions of the pattern go missing.

Images of the reflected pattern are acquired in sequences by a camera and processed by a computerized processing system that analyzes the variation in the pattern over time with a view to detecting deformations of the pattern and to deducing therefrom the time of appearance of film break-up regions.

Currently available devices that employ circular patterns and radial lines cause problems of a number of kinds:

on account of the shape of the test charts, and of the coverage of the cornea by disk sectors, spatial resolution is intrinsically worse at the edges of the field than at its center.

Moreover, at the center of the field, where the radial lines converge, it is difficult to determine the deformation of a pattern.

To increase spatial resolution the density of the pattern of the test chart must be increased. Furthermore, algorithms for detecting deformations of circles, which require most probable circles to be found in the image, whether a point in the image belongs to a probable circle to be evaluated and the distance of a given point to the circle to which it is supposed to belong to be computed, are complex and the processing and computing time taken to detect break-up regions on the basis of the image is substantial.

It will therefore be clear that: on the one hand, devices employing the conventional pattern of concentric circles and radial lines suffer from a lack of uniformity in spatial resolution, and, on the other hand, increasing resolution at the edge of the field adversely affects computing time.

Due to the low resolution of this method, the measurement may result in inaccurate and overestimated break-up times.

It will especially be noted that the measurements obtained using fluorescence methods and non-invasive methods are generally not well correlated: a factor of 2 difference between TBUT and NIBUT measurements is commonly observed, fluorescence methods returning a shorter time. This suggests that the devices used to measure NIBUT lack sensitivity or resolution.

Likewise, the NIBUT values measured using different available devices are also not well correlated.

In the diagnosis of dry eye syndrome, neither measurements (taken with fluorescein) of break-up time nor measurements of NIBUT are correlated with the suffering expressed by the patient.

The preceding methods do not reveal the overall state of the tear film, this being unhelpful to the practitioner who requires greater measurement accuracy and repeatability to carry out diagnosis.

SUMMARY

The present disclosure improves the situation and provides a method for measuring the stability of a tear film on the cornea of a patient, on the basis of detection of modifications of this film, using a device comprising a pattern made up of light and dark horizontal or vertical lines, and observation of the reflection of this pattern from the cornea.

To do this, in the context of the present patent application, micro-movements in the tear film are sought via analysis of the images of the lines of the test chart.

A local variation in the overall thickness of the tear film is called a micro-movement. This variation induces slopes in the surface of the tear film, which will be evidenced by a localized modification of the image of the lines of the test chart, and especially modifications of the width of the image of these lines or local deformations.

More specifically, the present patent application provides a method for measuring the stability of a tear film of a patient by means of a device comprising a backlit translucent plate equipped with a test chart that is positioned in front of at least one eye of a patient, and at least one digital photographic camera connected to a computing system provided with means for processing and analyzing images, an objective of the camera pointing toward the patient's eye in order to photograph a reflection of the pattern of the test chart from the patient's eye, characterized in that, the test chart being provided with a pattern consisting of a succession of alternating light and dark lines that reflect from the eye of the patient, the means for processing and analyzing images are configured to detect deformations of said light or dark lines of the pattern of the test chart reflected from the eye of the patient and to identify, via a comparison of the position of image points on the edge of the lines with respect to an estimated line edge of the lines, tear-film micro-movements revealed by these deformations, said method comprising, from a start time t0 at which an eyelid blinks, successively capturing images, successively detecting regions of micro-movement in the images and successively computing and storing data on the positions and number of regions of micro-movement of the tear film in each image by means of the means for processing and analyzing images, and computing, on the basis of the successively computed positions and number of regions of micro-movement of the tear film, a measurement of the average amplitude of the regions of micro-movement as a function of time.

This measurement has the advantage of providing an idea of the variations in the thickness of the tear film (film too thin or broken up locally) throughout a measurement sequence.

The features described in the following paragraphs may, optionally, be implemented. They may be implemented independently of one another or in combination with one another:

The method may comprise capturing (200) an image every 0.1 to 0.5 seconds and preferably every 0.3 seconds.

Said step of successively capturing images advantageously ends with the first occurrence of one of the following events: end of a time delay or detection of a next eyelid blink.

The method may comprise tracking the patient's eye or eyes by means of an iris-tracking method, so as to reposition the regions of micro-movement of the tear film that are detected and stored with respect to the analyzed eye.

The estimated line edges may be computed by polynomial regression.

The method may comprise determining a population of points representative of the regions of micro-movement observed in the image of the lines by computing, along the lines, the absolute value of the distance to the polynomial along the axis perpendicular to the general direction of the lines of pixels P1 to Pn of line edges of the image that are separated from the polynomial by a distance dP in pixels larger than a threshold, and storing, for the representative points P1 to Pn, the distances dP1 to dPn.

The method may comprise, for each image, for said population of representative points, computing, for each pixel P1 to Pn, the equivalent area Sp=dP×pixel width×pixel height, and computing the sum ΣSp of the equivalent areas SP1 to SPn from the image points to their polynomial over the entire image and computing a normalized sum NΣSp of said distances by means of division of the sum ΣSp by the total length of the lines found in the image.

The method may comprise computing an overall score consisting of the sum A of the normalized sums NΣSp over a series of images from the start time t0 to a given time t.

The length of the measurements may be chosen depending on a patient population, a length of the order of 6 seconds appearing to be sufficient to detect dry eye problems while avoiding the risk of blinking.

The method may comprise storing the positions of the regions of micro-movement and generating a map of the locations of the micro-movements image by image.

The method may comprise computing and storing the time of appearance of the points of micro-movement of the tear film and/or the rate of appearance of points of micro-movement of the tear film.

The method may comprise storing, in a database, all or some of the computed data with a view to monitoring the patient and comparing said data over a plurality of examinations.

According to another aspect, a computer program is provided that comprises instructions for implementing all or some of a method such as defined herein when this program is executed by a processor.

According to another aspect of the present disclosure, a computer-readable non-volatile storage medium is provided on which is stored such a program.

The present disclosure and the variants thereof may allow, generally, a method for measuring the variation in irregularities in a tear film over a defined examination period to be provided, which method is more accurate than existing methods for detecting break-up of such a tear film.

Such a solution, which is based on a measurement of deformations of the film and their variation over time, allows the problems posed by the known solutions to be solved while achieving a high measurement repeatability.

BRIEF DESCRIPTION OF THE DRAWINGS

Other features, details and advantages of the present disclosure will become apparent on reading the detailed description that follows, and on analyzing the appended figures in which.

DETAILED DESCRIPTION

The drawings and the description below describe one or more examples of embodiment that will therefore possibly not only be used to better understand the subjects of the present patent application, but also contribute to its definition, where appropriate.

Figure 1:
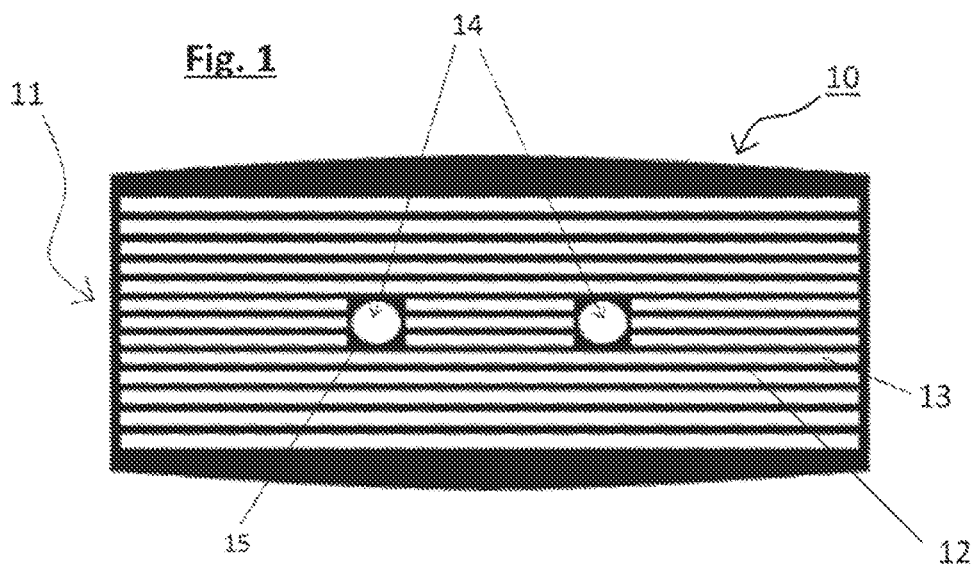
FIG. 1 is a plan face-on view of a test chart provided with a pattern of the present disclosure.

The method according to the present patent application uses a measuring device comprising a test chart 10, shown in FIG. 1, that is produced with a transparent polymer film comprising a pattern 11 made up of alternating straight and parallel lines 12, 13. The pattern comprises opaque lines 12, black lines for example, separated by transparent lines 13 that let pass the light of a light source, which passes through a translucent carrier behind the pattern, so as to produce light lines, the light lines of the pattern being reflected from the eye or eyes of a patient.

In this example, the pattern 11 of the test chart 10 comprises twelve opaque lines 12, excluding the top and bottom borders of the test chart. These opaque lines are separated by transparent lines 13 and centered on a translucent median line. The test chart may be mounted on a plastic frame in order to make it easier to handle.

By convention, an axis parallel to an axis passing through the patient's eyes will be called the horizontal axis, and the axis perpendicular to this axis will be called the vertical axis; in the illustrated example, the lines of the pattern are horizontal.

Figure 2:
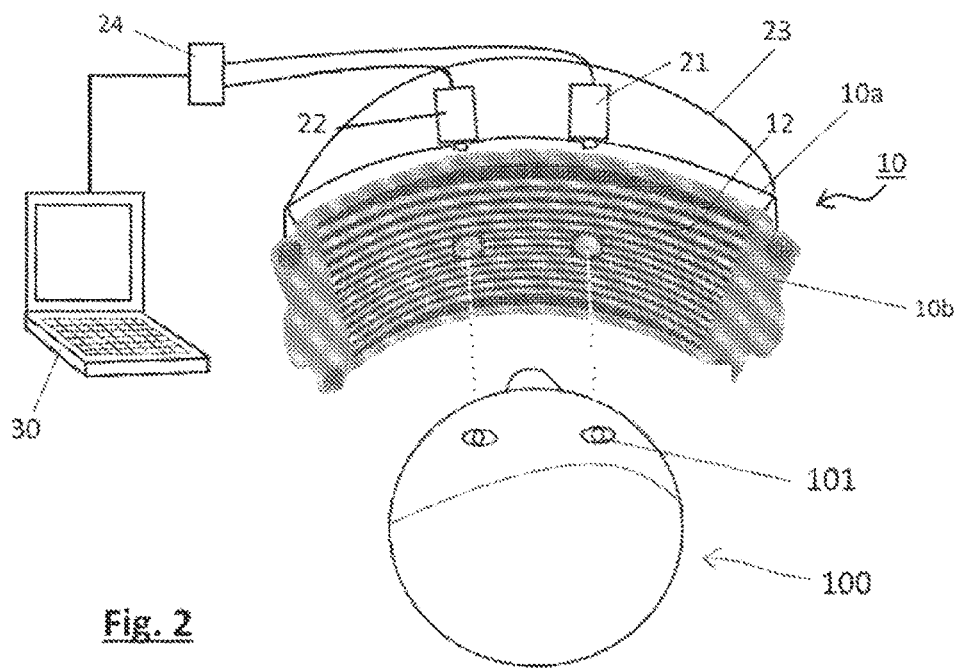
FIG. 2 is a schematic view of a device of the present patent application.

As shown in FIG. 2, the test chart 10 on its plastic carrier 10b is positioned on a translucent carrier 10a itself drilled with holes for passage of camera objectives, and the device uses a diffuse light source 23 behind the carrier of the pattern to illuminate the pattern. The reflection of the pattern is observed by one or two digital cameras and, to observe both eyes, two digital cameras 21, 22 are provided.

The diffuse light source 23 may be produced by means of an integrating box or sphere or similarly to an LCD backlight for example.

The test chart is provided with two empty regions 14 centered in opaque frames 15 on a horizontal median line. The empty regions are separated by a distance corresponding to an average interocular distance, as shown in FIG. 1. Returning to FIG. 2, the cameras are positioned behind the empty regions and in front of the eyes 101 of the patient 100. The objectives of the cameras film or photograph the patient's eyes through the empty regions. The empty regions may be replaced by transparent substrate regions of the test chart if the optical properties of the substrate of the test chart and its level of cleanliness are compatible with image formation (transparent and non-scattering).

The cameras are for example CMOS cameras with ¼" sensors. According to the non-limiting example shown, the transparent regions are circular holes of a diameter suitable for the objectives of the cameras. For cameras with optics of focal length of the order of 4 mm, holes of the order of 14 mm are provided and the opaque frames are opaque squares of the order of 16 mm×16 mm. The aim of these frames is to precisely terminate the lines upstream of the holes that receive the objectives of the cameras.

In this example of embodiment, the one or more cameras deliver images with a definition of 1920×1080, which is sufficient to obtain an analysis of the tear film without unduly increasing the computational load on the system.

The video signals or the signals of the cameras are sent to a computerized processing device 30 or computing system that is either internal or external to the measurement device, and, to avoid duplication of this processing device, the video signals of the two cameras are passed, via a multiplexer, on an electronic board 24 of the device, the multiplexer allowing either of the video channels to be sent to the processing device 30 as desired.

The cameras film or photograph the image, of the lines of the pattern, reflected from the patient's cornea. As the cornea, to a first approximation, may be considered to be a spherical dioptric interface, it has a high field curvature, and the image exhibits substantial distortion. In order to at least partially compensate for this distortion and to ensure, in the captured images, that the width of the lines varies little from the median axis of the pattern to the edge of the image, the pattern of the test chart comprises lines the period of which increases from the central axis of the pattern to the edges of the carrier that are parallel to the lines. The width of the lines is of the order of 2 to 4 mm, depending on the desired resolution. For example, a central white line may have a height of about 2.8 mm, the adjacent black lines a height of 2.2 mm, while the last white lines have a height of 3.8 mm and the black lines preceding these white lines have a height of 2.8 mm, the progression being optimized to compensate for the curvature of a standard eye. In the described method, it is the light lines that are exploited to find the width variations or deformations of the lines, but the dark lines may also be used. The number and width of the light lines may be different from the given examples, but are chosen to obtain a definition sufficient to achieve a meaningful detection of the regions of deformation of the film given the resolution of the one or more cameras.

In the context of the present patent application, the white lines are reflected by the corneal dioptric interface and stand out whereas they are backscattered from the bulbar conjunctiva of the eye and the iris, the backscattered alternation of dark lines and light lines in contrast forming a continuous background the brightness of which depends on the ratio between the transparent area of the test chart and its total area.

In FIG. 2, the test chart, seen from above, is curved about a vertical axis to form a portion of a cylinder and to follow the curvature of the patient's head 100 so that the image of the test chart covers most of the cornea.

The reasons therefor are:

a. Optical conjugation:
   The camera sees the reflection of the test chart from the cornea, which is considered, to a first approximation, to be a spherical mirror with a radius of about 8 mm, or 4 mm focal length. Given this short focal length, the test chart (the object in the optical conjugation) must be large for the size of the image reflected by the cornea to be large enough, i.e. comparable in size to the outside diameter of the iris. This is what determines the size of the mask.

b. Photometry:
   For the test chart to be visible, light rays from the extreme edges of the test chart must enter the pupil of the objective. Since the cornea is a mirror of high curvature, it is necessary, on the field edge, for the light rays reaching the cornea to be grazing.

This is what justifies the curvature of the test chart.

Figure 3:
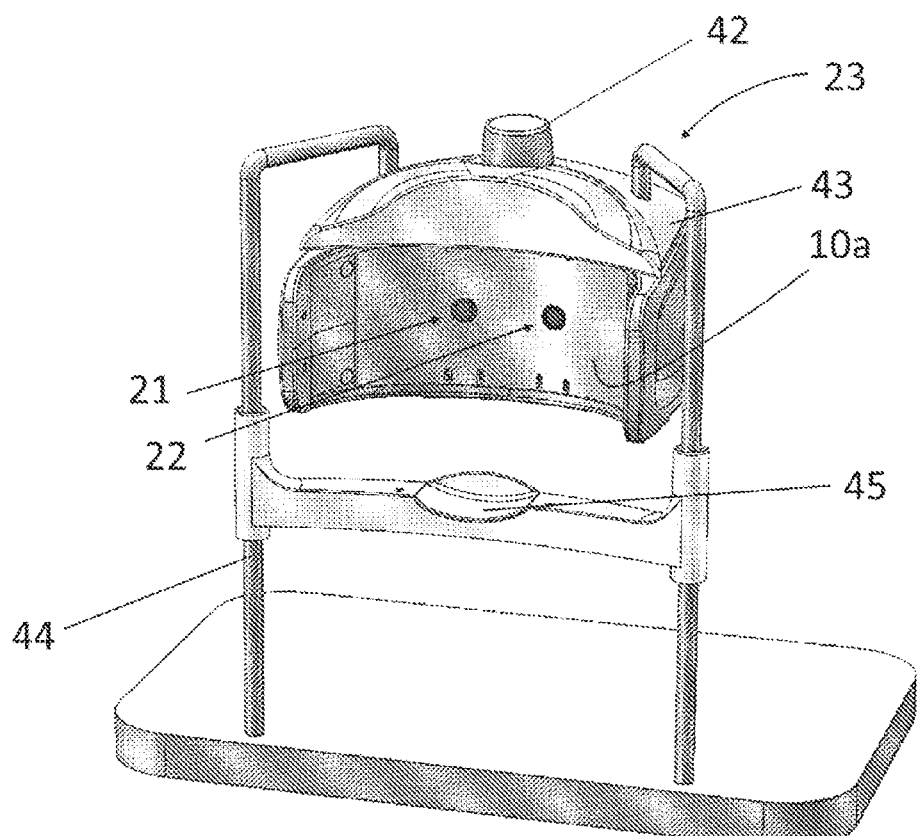
FIG. 3 shows a first example of measurement apparatus usable in the context of the present patent application.

In FIG. 3, the measuring device is mounted on an ophthalmological structure with a chin and forehead rest, the structure comprising uprights 44, 46 and a casing 43 into which are integrated the cameras and that receives the test chart 10 on a frontal curved face in front of which the patient places himself, chin resting on a support 45. With such a structure, the patient's eyes are at a distance from the test chart of about 50 mm for a camera of 4 mm focal length. The measuring device may also be integrated into a headset worn by the patient.

Allowing for variations in the position of the eye with respect to the camera (different interocular distance from one individual to the next) the focal length and the distance are chosen to permit the whole eye to be seen. Next, a window of interest centered on the patient's pupil is chosen, via an action of the operator, who marks the center of the pupil in the image.

So that the lines of the test chart are sharp in the image, the focus is adjusted with a thumbwheel 42.

The object of the measuring method of the present patent application is to detect and measure extents and regions of instability in the tear film, which result in deformations of the reflected lines. The measuring method comprises repeatedly capturing images of one or both eyes of the patient at a repetition rate of the order of 0.1 to 0.5 seconds and in practice of 0.3 seconds, after a blink of the eyes or of the eye.

The method is mainly described in the context of a test chart composed of lines that are horizontal, i.e. that extend along an axis passing through the two pupils of the patient, but is adaptable, especially by means of a 90° rotation of the means for processing series of pixels and of the anisotropic band-pass filter described below. Moreover, the method, which is described in the context of detection of light lines, is applicable to detection of dark lines.

Using horizontal or vertical lines rather than inclined ones is advantageous because it is easier to carry out image processing along rows or columns of pixels.

Figure 4:
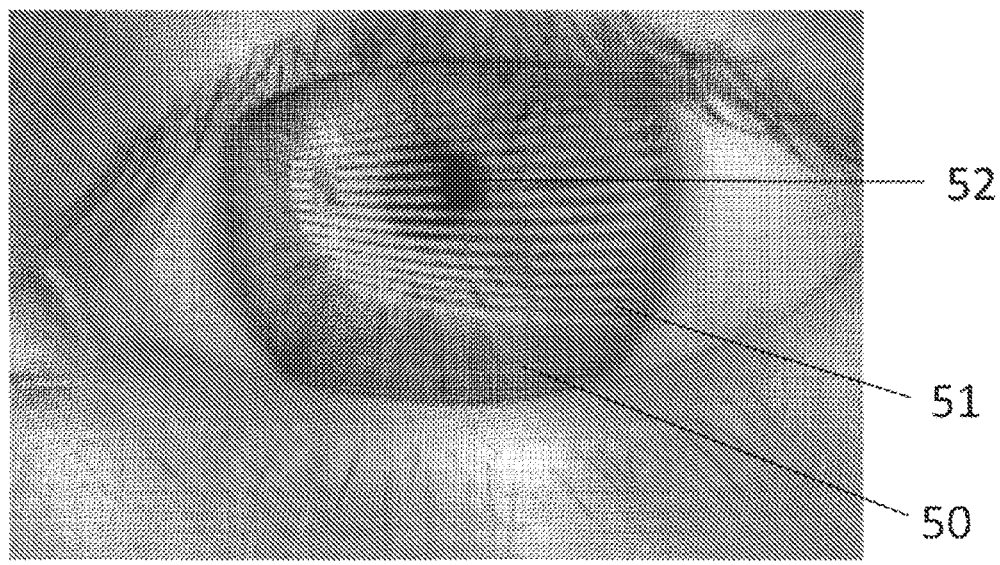
FIG. 4 shows an image of a patient's eye following a first treatment step.
Figure 5A:
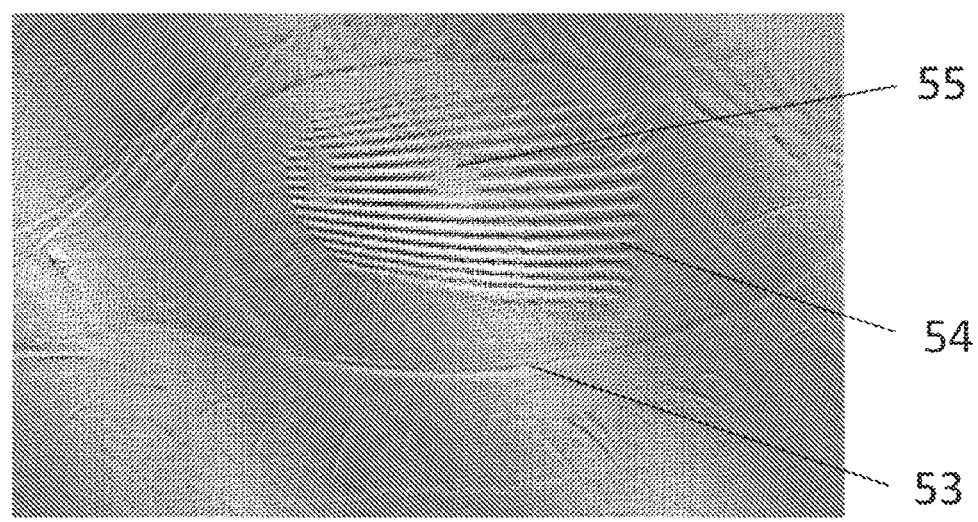
FIG. 5A, FIG. 5B, FIG. 5C, FIG. 5D and FIG. 5E show various stages of processing the image of the eye of FIG. 4.

In the computing system 30, the measuring steps comprise image-processing steps that, starting from capture of the original image of the patient's eye, comprise:

converting (step 205 of FIG. 12) the image into grayscale, an example of the result of which is shown in FIG. 4 in which may be seen the image 51 of the pattern on the iris 50 with the image of the frame 52 encircling the objective of the camera. In this image and in the original color image, the shape of the reflected light lines comprises local defects (especially irregular line edges that alone imply deformation of the tear film);

applying (step 210 of FIG. 12) a band-pass filter that is anisotropic in a direction perpendicular to the direction of the reflected lines. This direction is a vertical direction, direction of the columns of pixels of the image, in the case of a test chart composed of horizontal lines, or of a test chart composed of vertical lines with the image rotated by 90° to obtain light lines oriented in a horizontal direction. The filter is configured to pass abrupt transitions between grayscale levels and to remove or attenuate modulations of low spatial frequency and of higher spatial frequency in the perpendicular direction. The image output from the filter is shown in FIG. 5A. This filter especially has the advantage of removing vignetting and defects in lighting uniformity. This transformation accentuates the edges of the eyelid 53, the light lines 54 of the pattern of the test chart and preserves the image of the frame 55.

Figure 5B:
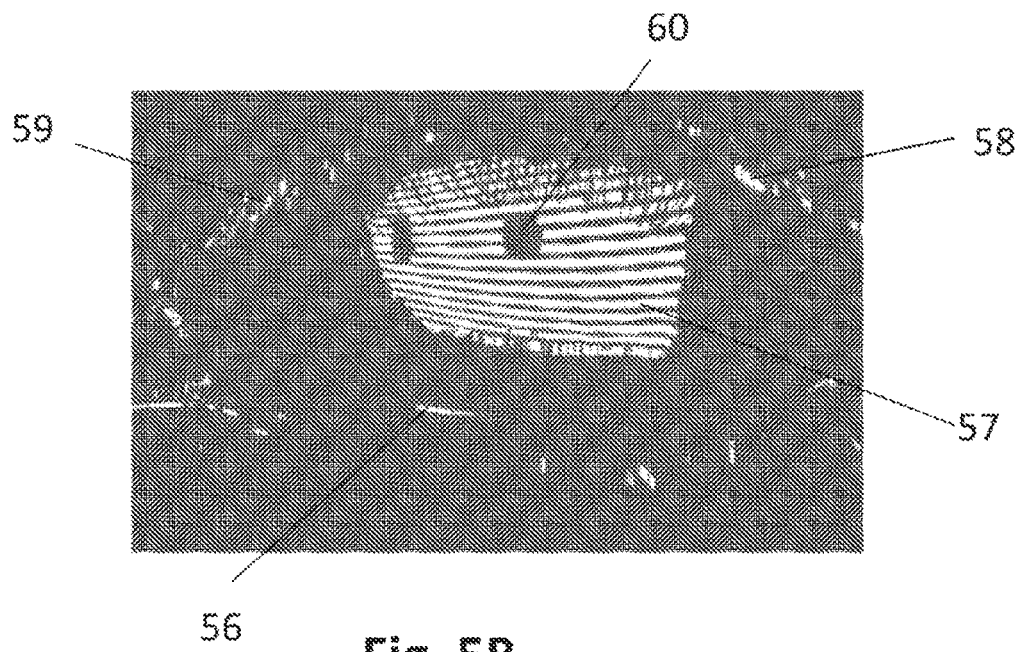
Figure 5C:
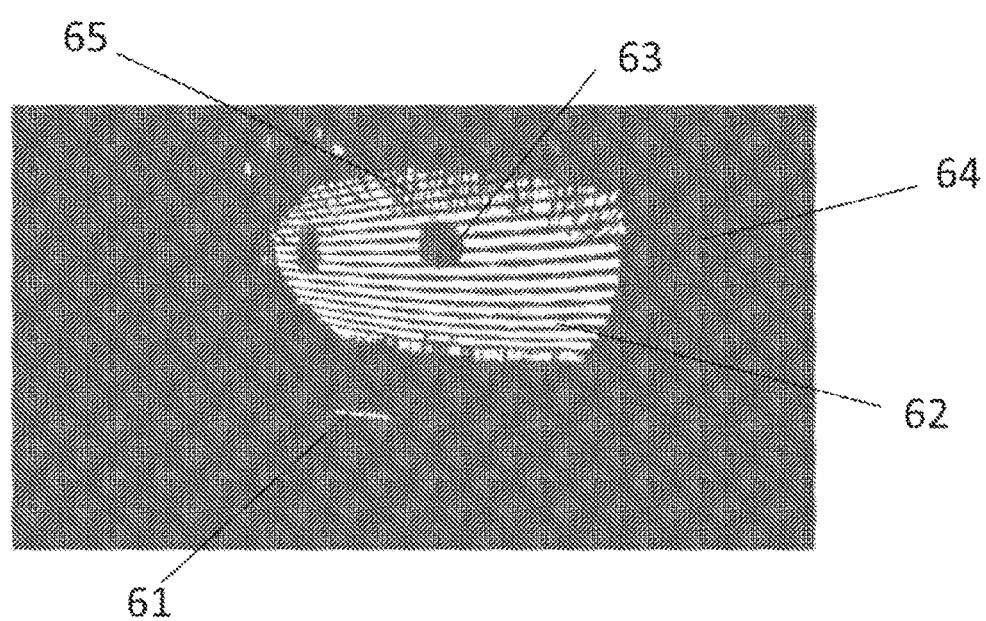
Figure 12:
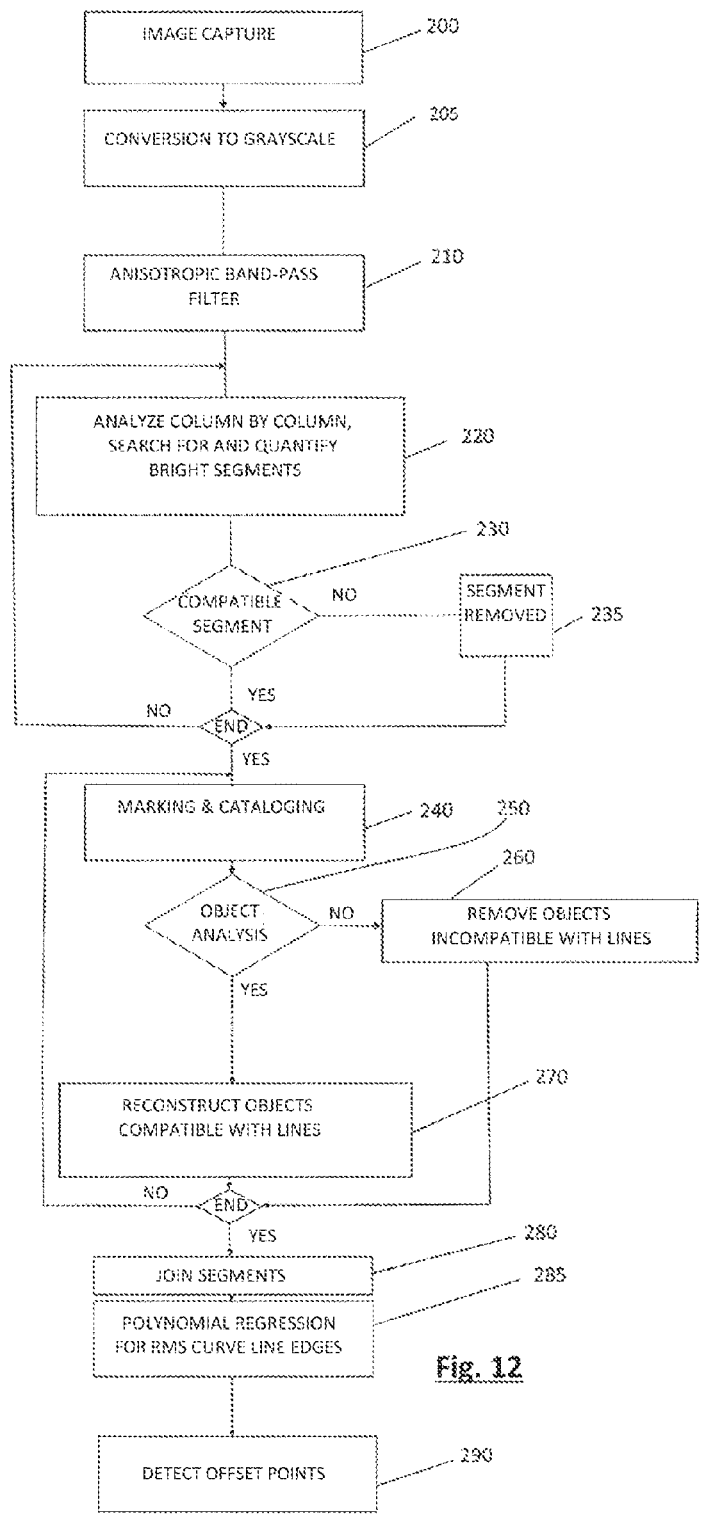
FIG. 12 schematically shows a method for detecting offset points according to one aspect of the patent application.

Next, again in the case of light lines oriented in a horizontal direction, the method comprises analyzing 220 the image in columns of pixels, as shown in FIG. 12, to search for bright vertical segments. The resulting image then comprises lines 56, 57, 58, 59 as shown in FIG. 5B. Once this analysis has been carried out, the bright segments are qualified by their size, in steps 230 and 235. This allows segments that are too large or too short, and that clearly do not correspond to segments of lines of the pattern, as for example is the case of segments forming part of the outline of the eyelids, to be removed. FIG. 5C shows, at the end of this step, the image, in which the column segments of the isolated line 61, the lines of the image of the pattern 62, the background 64 and the frame 63 remain. It will be noted that the eyelashes cause a substantial fragmentation of the lines 65 at the top of the image. In the case of a test chart composed of vertical lines, the segments are analyzed and qualified in rows of pixels.

Figure 5D:
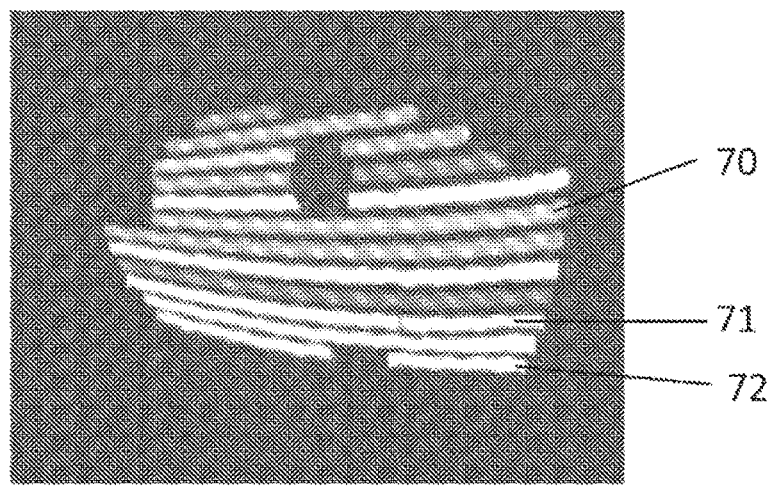

When the segmentation has ended, the processing method comprises an algorithm for marking/cataloging 240, 250, 260 the bright segments to obtain objects representative of bright lengths of lines of the pattern and to reject bright objects not having the desired shape, which are thus considered artifacts. This algorithm firstly joins contiguous column segments to reconstruct horizontal lengths. The result of this marking/cataloging is shown in FIG. 5D, in which each line found has been assigned a color here represented in grayscale. This cataloging allows complete lines 70 or isolated lengths 71, 72 to be created.

Figure 5E:
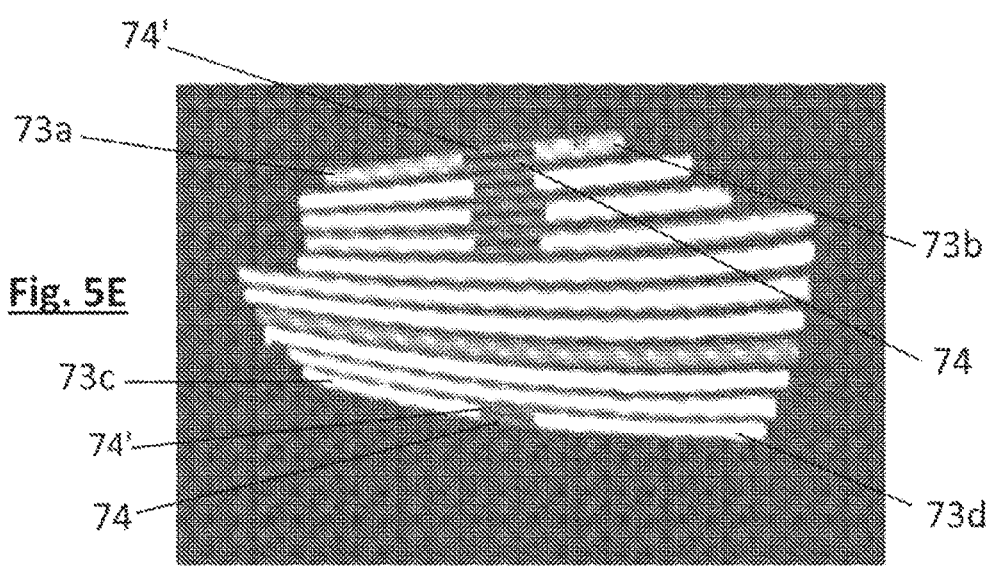
Figure 6A:
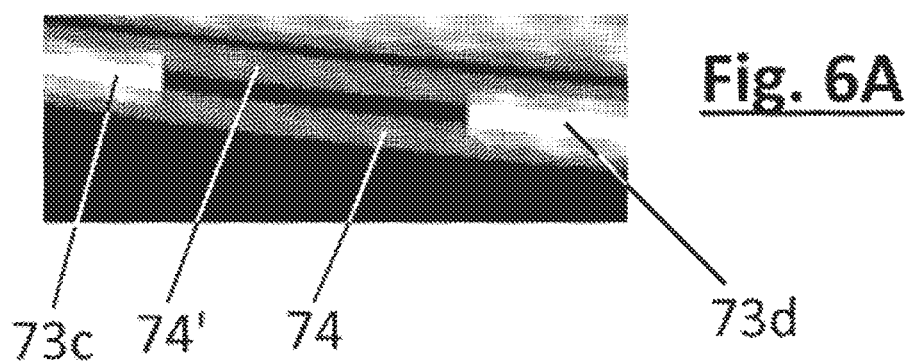
FIG. 6A and FIG. 6B show details of FIG. 5E.

In a subsequent step, the lengths of bright lines of same level (for example of similar width and altitude) in the image are joined, then a polynomial regression 285 using a polynomial of order higher than two is applied so as to compute an RMS curve of the shape of the line edges. This step is shown in FIG. 5E. In this figure it will especially be noted that lengths 73a, 73b of the lines fragmented by the image of the frame encircling the objective of the camera, and lengths 73c, 73d of the bottom line, have been joined by bottom 74 and top 74' RMS curves. The enlargement of FIG. 6A allows the RMS curves 74, 74' between the lengths 73c, 73c at the bottom of the image to be seen more clearly. Next, offset points are detected 500, in places where the edges of the lines comprise measurement points that deviate from the shape given by the polynomial.

Contrary to a method in which confirmed film break-ups are simply sought, in the context of the present disclosure, fluctuations in the thickness of the film are sought, these resulting in micro-movements in the film.

With respect to detection, the criterion taken into account is here merely a threshold criterion (for example a threshold of one pixel) for filtering out noise in the image, all deviations between points and the polynomial larger than this threshold being taken into account.

Figure 6B:
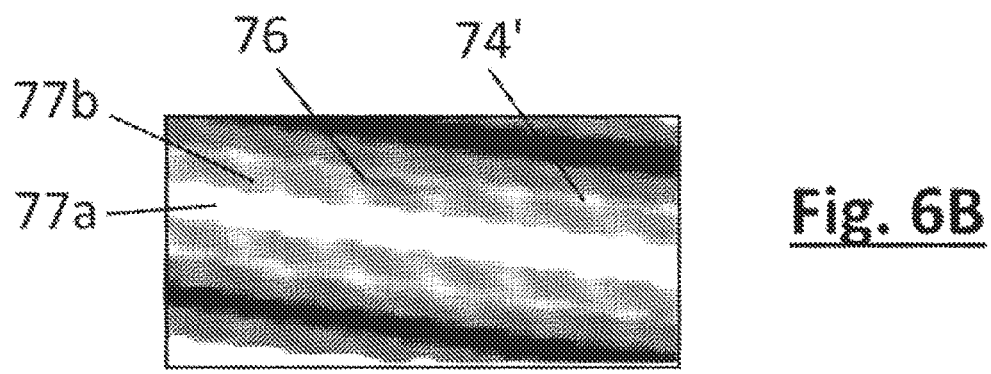

This is for example shown in FIG. 6B in the region 76 in which the line edge 77b of line 77a does not follow the curve 74'.

As seen above, the method may be based on processing of dark lines. Grouping pairs of transitions (rising and falling transitions in the case of light lines) allows the consistency of the width of the obtained segment to be checked and segments that are too wide or too narrow to form part of the image of the test chart to be rejected. Once the lengths have been determined, the polynomial regression is performed on each side of the length: one polynomial for the rising transitions, one polynomial for the falling transitions. The method of the present disclosure may therefore equally well target dark segments and dark lines, the same polynomial regressions and the same final result being obtained.

Figure 7:
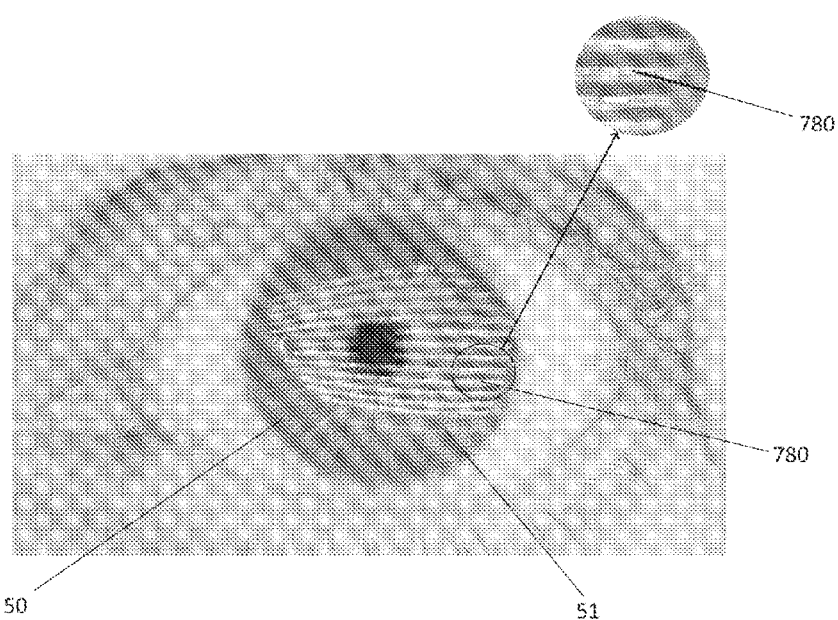
FIG. 7 shows an image of the eye of FIG. 4 after image analysis.

The result of the measurements is a map of micro-movements in the tear film, a map of this type being shown in FIG. 7, which figure is a view of a patient's eye 6 seconds after blinking, with an enlargement, and in which figure the map of regions 780 of small or zero film thickness appears positioned on lines 51 in the initial color image of the eye, which image is here shown in grayscale.

The micro-movements correspond to progressive local sagging or deformations of the film, which for example take the form of depressions that may go as far as to break up the film and that result in deformations of the lines since they modify the curvature of the dioptric interface locally. The variation in these deformations when the eye is observed with magnification appears in the form of micro-movements or undulations.

As seen above, images are captured about every 0.3 seconds. A start time is defined by an eyelid blink and, repeating the measurement for each image over a time period allows a map of defects in the tear film as a function of time to be constructed.

One problem to be considered is that the patient's gaze may change direction during the image-acquisition period.

Since the camera observes reflections of the pattern from the cornea, which to a first approximation behaves like a spherical dioptric interface, the position of the image of the pattern remains almost invariant in the image delivered by the camera, whereas the position of the iris changes if the patient turns his eyes. Thus, a given point of the image of the test chart is not tied to a fixed point of the cornea, but rather to a point dependent on the direction of the gaze. This implies that the measurement must be referenced with respect to the position of the observed eye and not with respect to the image of the pattern.

To do this, the position of the eye in each image has to be tracked. It is preferable to follow the outline of the iris of the eye because it contrasts highly with the bulbar conjunctiva, which is light in color and from which there is no reflection of the test chart, the pupil being trickier to follow due to the reflection of the test chart, which complicates analysis of the image.

The following method may be implemented in the context of the present patent application or independently to perform other measurements on the eyes. This method is moreover independent of the orientation of the lines of the test chart.

FIGS. 8, 9A, 9B and 9C correspond to processing operations carried out on images of an eye of a patient looking at the camera, and FIGS. 10, 11A, 11B and 110 correspond to processing operations carried out on images of an eye of a patient whose gaze has deviated from the camera.

Figure 8:
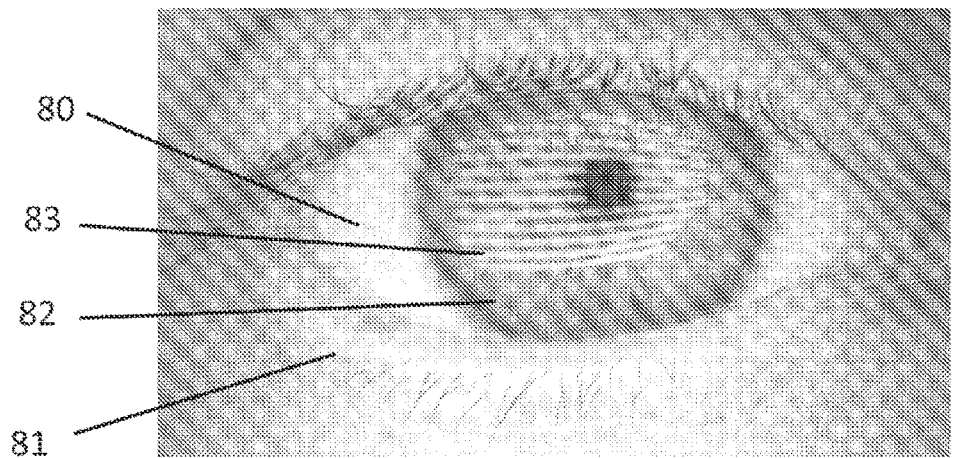
FIG. 8 shows an image of an eye of a patient looking toward a camera.
Figure 9A:
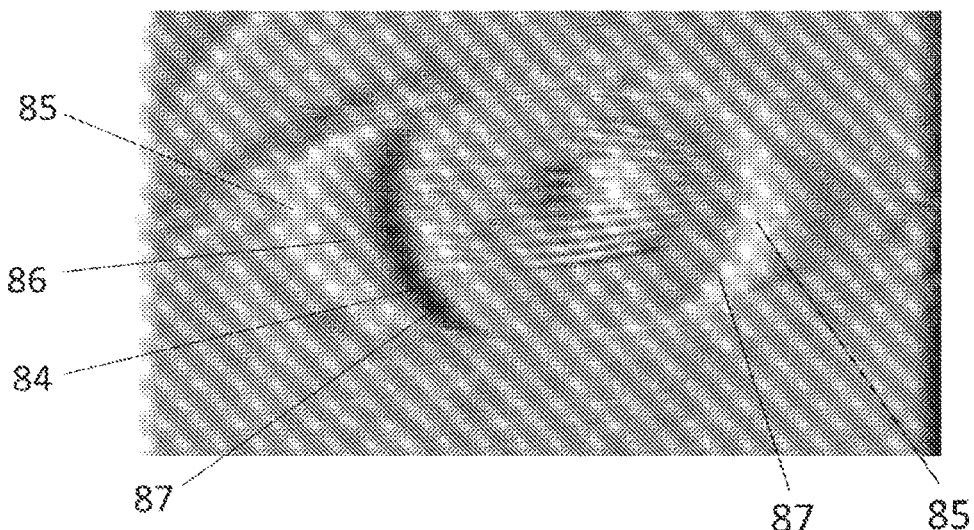
FIG. 9A, FIG. 9B and FIG. 9C show steps of determining the position of the iris of the eye of FIG. 8 according to one aspect of the patent application.
Figure 9B:
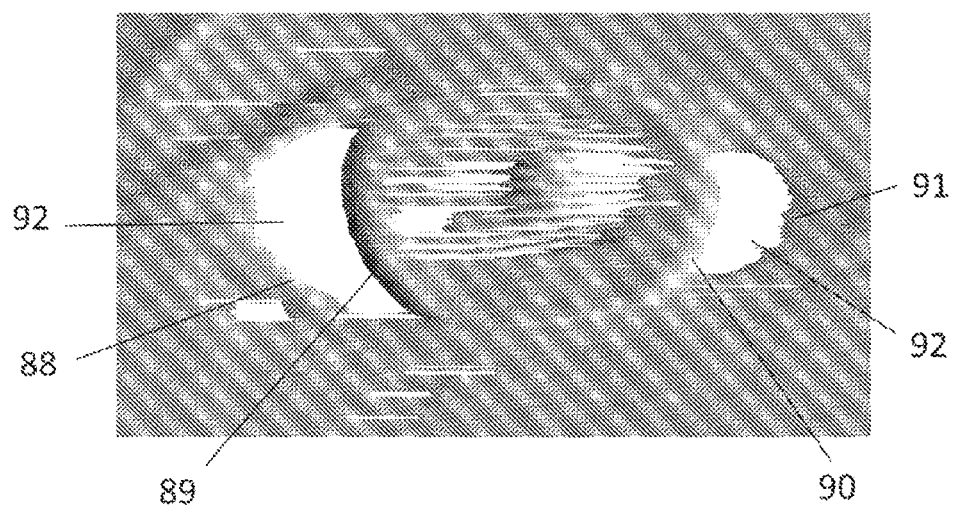
Figure 9C:
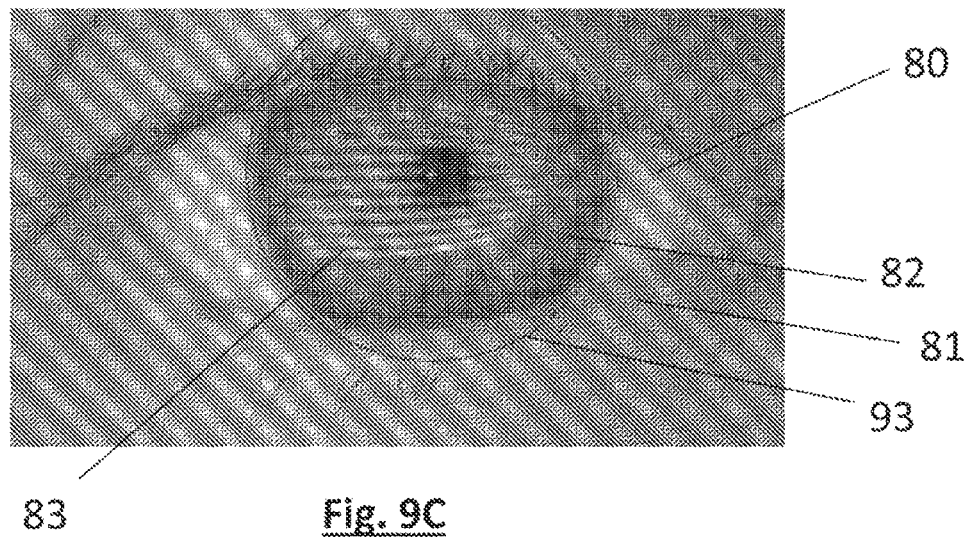

In FIG. 8, the eye 80 is looking straight ahead, and the image of the pattern 83 is centered with respect to the iris 82, which itself is centered with respect to the eyelid 81.

Figure 13:
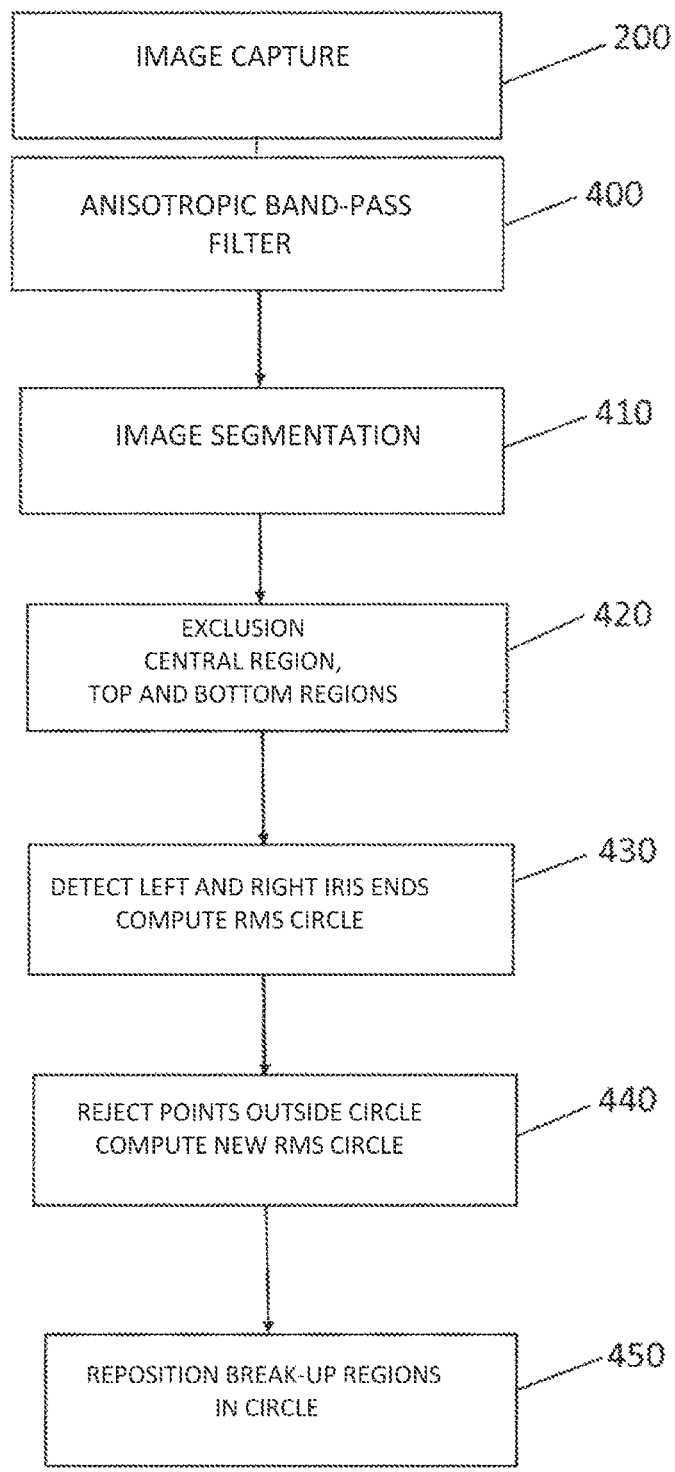
FIG. 13 schematically shows a method for repositioning deformations of image lines of a test chart.

The image-processing method employed to find the position of the iris is schematically shown in FIG. 13. It comprises a first transformation of the image, achieved via application of an anisotropic band-pass filter 400, which is applied horizontally so as to detect transitions in brightness along a horizontal axis. In this operation it is sought to distinguish between falling transitions (light to dark) and rising transitions (dark to light) and, for the sake of legibility, light-to-dark transitions (falling transitions) have been represented by dark crescents 84 in the grayscale image in FIG. 9A and dark-to-light transitions (rising transitions) have been represented by light crescents 85 in FIG. 9A. Portions of the image in which there are no significant transitions, such as the crescent 86 for example, become an average gray, and the outline of the iris is manifested by a ring portion 87 that is located, on the left-hand side, next to a light-to-dark transition and, on the other side of the eye, next to a dark-to-light transition.

Returning to FIG. 13, a second operation consists in segmenting the image 410 with a view to finding pairs of rising and falling transitions (84, 85 in FIG. 9A for example) forming the borders of bright regions in the image, especially around the bulbar conjunctiva. These pairs of transitions, indicated by the limits 88, 89 and 90, 91 in FIG. 9B, frame regions 92 potentially defining the bulbar conjunctiva.

After this transformation, the method comprises, as shown in FIG. 13, filtering the image 420, which removes the central region comprising the pattern and the top and bottom regions of the image. On the basis of the remaining parts, an RMS circle is computed for the perimeter of the iris, from the right ends of the left-hand segments of the image and from the left ends of the right-hand segments of the image 430. For this computation, points too far from the RMS circle, which correspond to imperfections especially caused by the eyelashes or the eyelid, are rejected in step 440 and, as regards the remaining points, a new RMS circle is computed to follow the outline of the iris, this circle 93 being shown in FIG. 9C on the original image of the eye.

Figure 10:
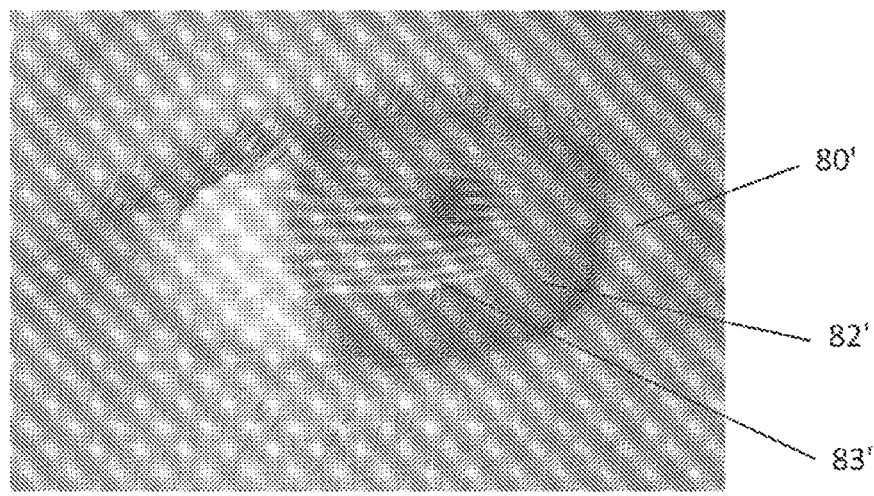
FIG. 10 shows an image of an eye of a patient whose gaze has deviated from a camera.
Figure 11A:
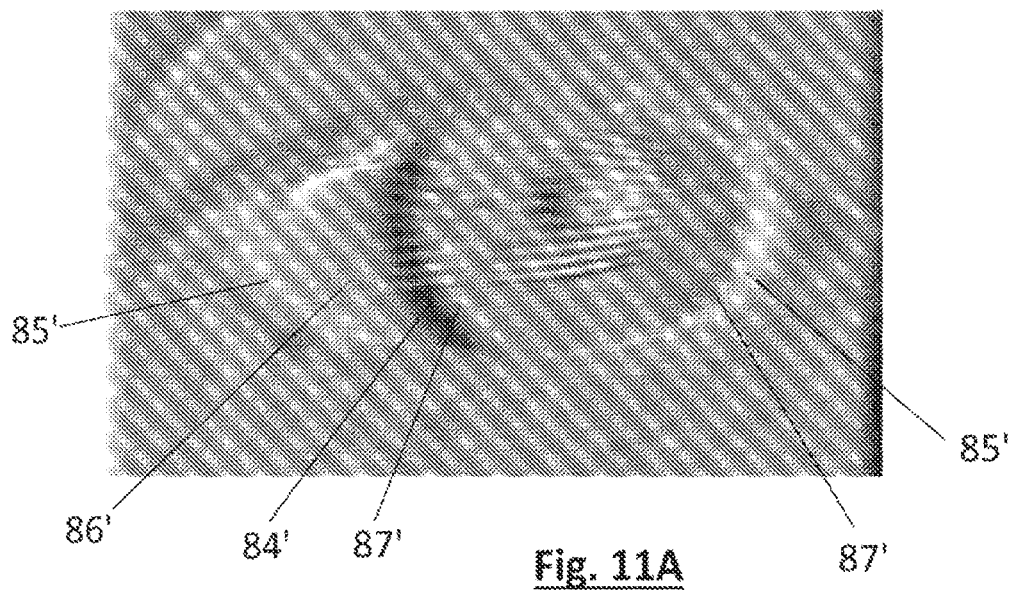
FIG. 11A, FIG. 11B and FIG. 11C show steps of determining the position of the iris of the eye of FIG. 10 according to one aspect of the patent application.
Figure 11B:
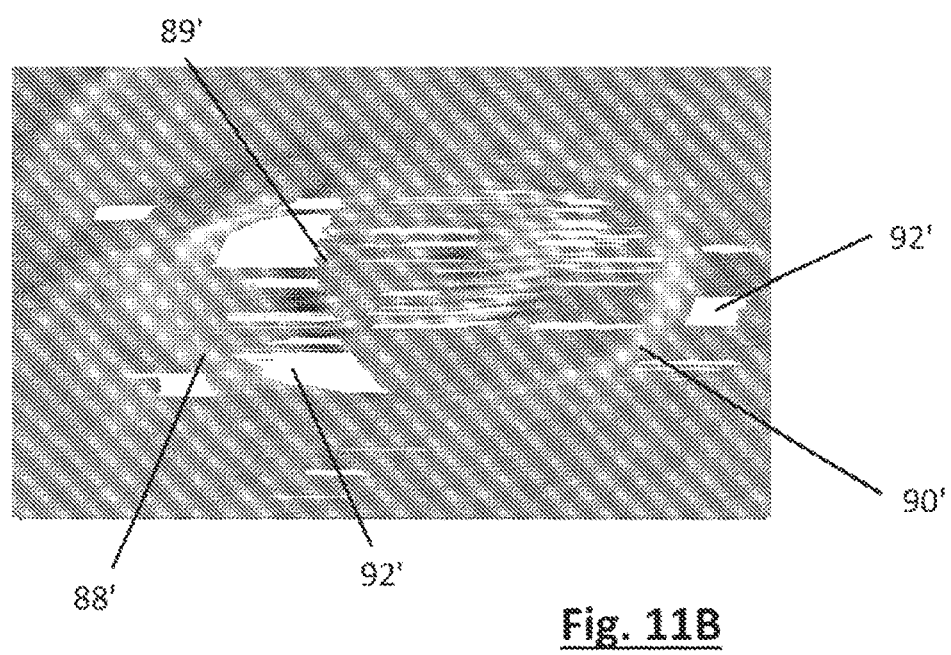
Figure 11C:
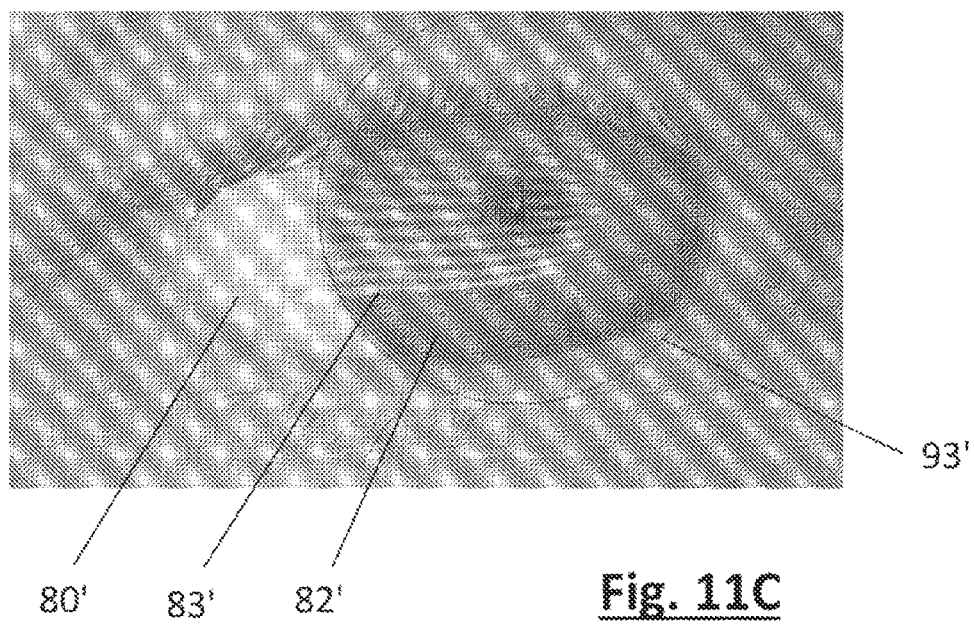

FIG. 10 shows an eye 80' looking sideways and the iris 82' of which is offset with respect to the pattern 83'. For this position of the eye, the transitions 84', 85' around dark regions 86', 87' corresponding to uniform colors are offset laterally in FIG. 11A, though in FIG. 11B it may be seen that the circular arcs 89' and 90' corresponding to the edge of the iris remain detectable. Application of the tracking method once again leads to recreation of the RMS circle 93', which will be repositioned in the original image as shown in FIG. 11C. The detected regions of deformation are then relocated, in step 460, depending on the position of the circle defining the outline of the iris. This makes it possible to anchor the deformations of the tear film to the outline of the eye, rather than to the image.

This sequence is carried out for each image, preferably after the analysis of the line pattern described above.

As stated above, this method is here applied to reposition the deformations of the film, but it may also be used for other types of detection and methods that require the position of an eye to be tracked.

According to one aspect of the patent application, the device may comprise a manual trigger that arms the device, the sequence of image captures then being triggered on the occurrence of an event such as a series of two blinks of the eyelids of the patient. To do this, the system comprises a method for recognizing a blink of the eyelids, which allows the measurement sequence to be started automatically. Likewise, the system may stop the sequence of measurements automatically, on detection of a subsequent blink of the eyelids, or stop the sequence automatically after a time delay, of 15 seconds for example.

The sequence of image captures may comprise from 30 to 50 images for example, and in the case of a sequence of image captures of 15 seconds length with images captured every 0.3 seconds the sequence comprises 45 images. The images may be analyzed after the sequence of image captures and, because of the chosen solution, i.e. the choice to work with a pattern made up of lines, the processing time remains low, for example 15 seconds with a standard computer.

Figure 14:
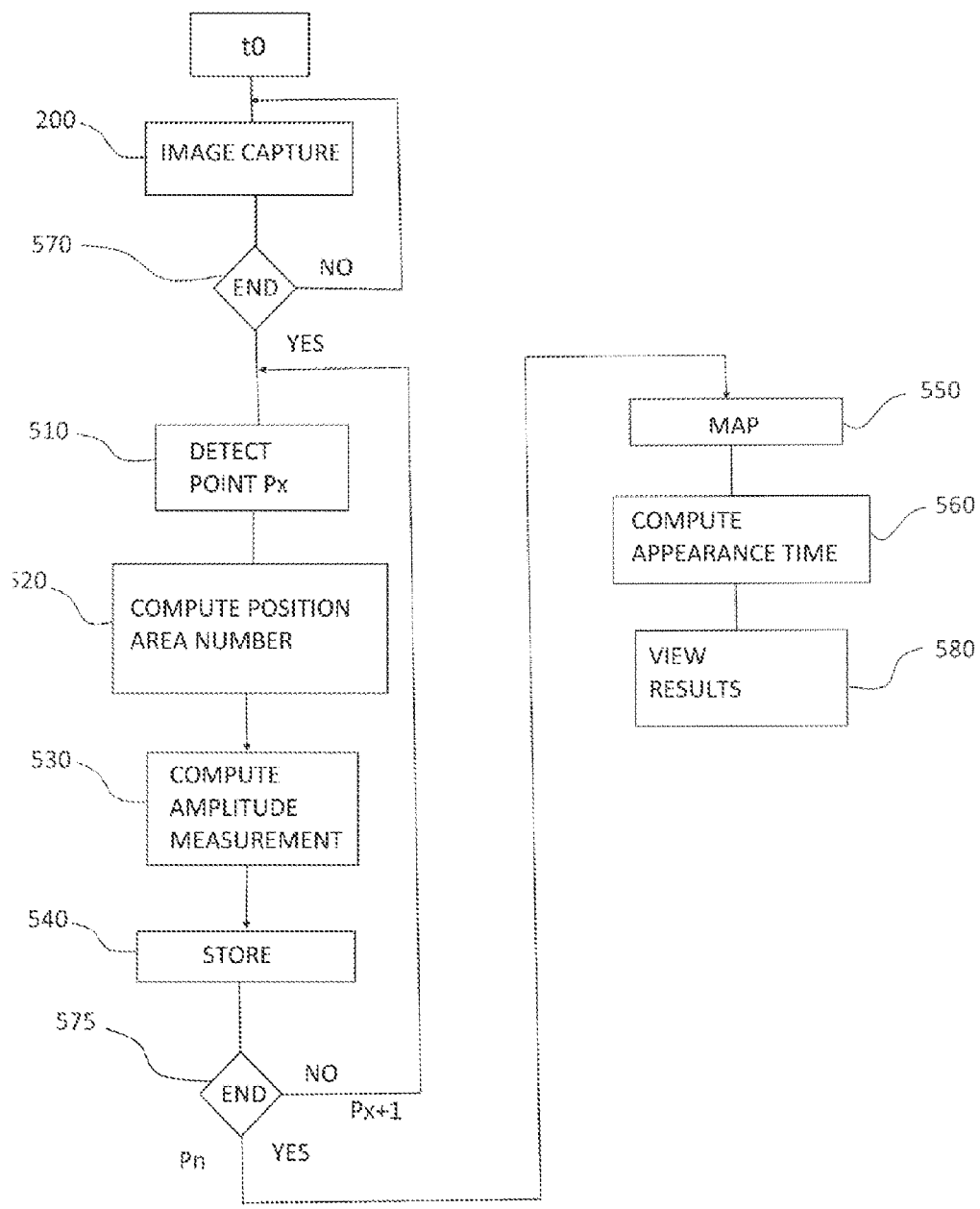
FIG. 14 schematically shows first steps of the method of the patent application.

In FIG. 14, the method comprises, from a start time t0 at which an eyelid blinks, successively capturing 200 images over a sequence that will last about fifteen seconds and during which images are captured every 0.1 to 0.5 seconds and preferably every 0.3 seconds to obtain a good compromise between the detection of variations in the tear film and the quantity of data to be processed.

The succession of image captures ends 570 with the first occurrence of one of the following events: end of a time delay, for example 15 seconds, resulting in 45 images if one image is captured every 0.3 seconds, or detection of a next eyelid blink.

Between the image captures or in a replay mode, i.e. in non-real time, the method comprises successively detecting 510 regions of micro-movement in the images and successively computing and storing 520 data on the positions, area and number of regions of micro-movement of the tear film in each image by means of the means for processing and analyzing images, for example according to the method for FIG. 12 and especially using polynomial regression, which will make it possible to determine estimated line edges by means of a polynomial-regression polynomial.

The method then comprises the computing 530 and storing 540 of a measurement of the amplitude of the regions of micro-movement as a function of time. This measurement provides insight into decreases in the thickness of the film across the entire extent of the imaged lines.

To readjust the positions of the lines between images, the method will track the patient's eye, this tracking being the subject of FIG. 13.

Figure 15:
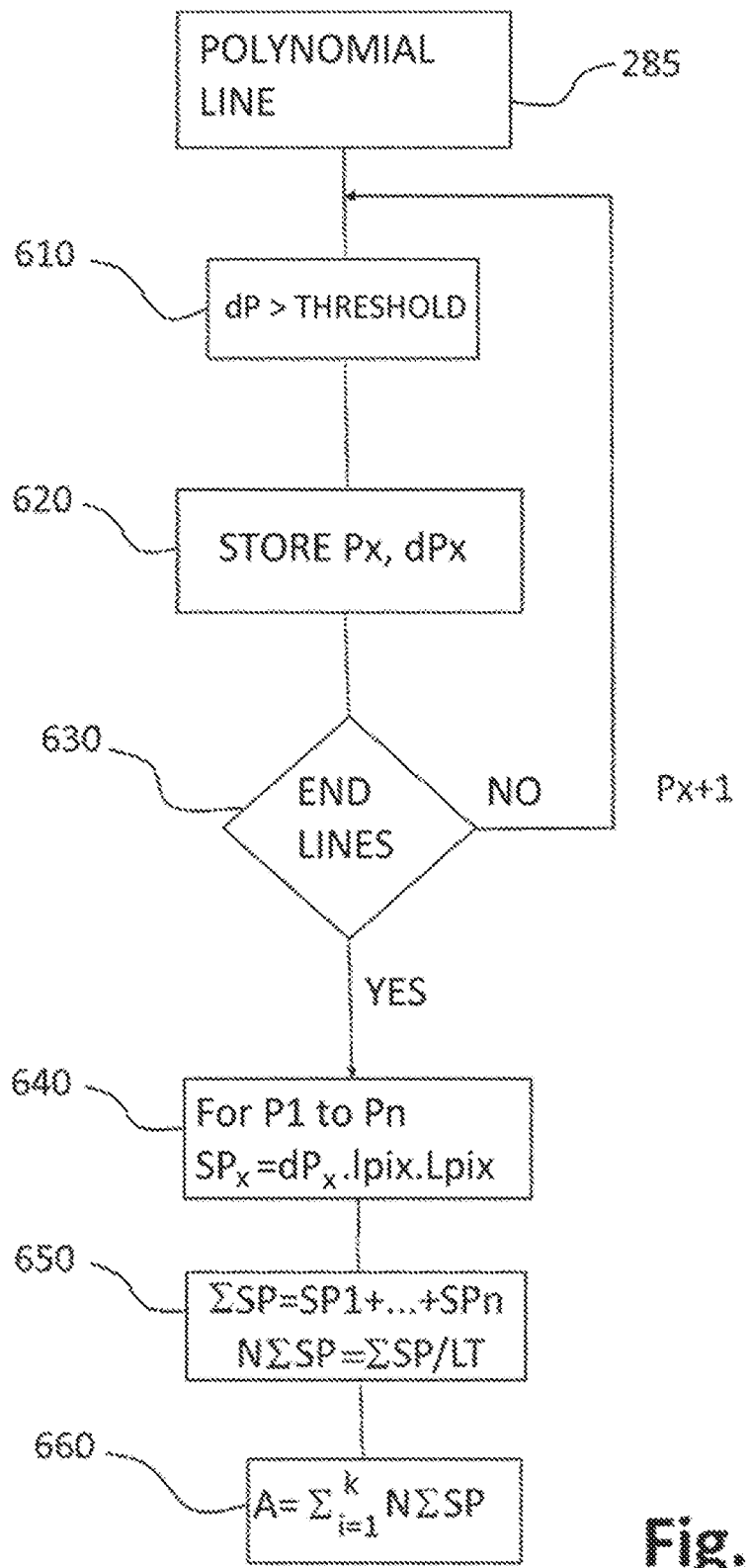
FIG. 15 schematically shows subsequent steps of the method of the patent application.

In a following step, as shown in FIG. 15, the method will allow a population of points representative of the regions of micro-movement observed in the image of the lines to be determined.

This is done by computing 610, along the lines, the absolute value of the distance to the polynomial along the axis perpendicular to the general direction of the lines of pixels P1 to Pn of line edges of the image that are separated from the polynomial by a distance dP in pixels larger than a threshold 620. These representative points P1 to Pn and the distances dP1 to dPn are then stored. In the case of horizontal lines, the distance is vertical and in the case of vertical lines, the distance is horizontal.

To determine an extent of the regions in which the film is deformed, the method comprises, for each image, computing 640, for each pixel P1 to Pn, the equivalent area of the deformation in the line edge, i.e. Sp=dP×pixel width×pixel height.

Subsequently, the following are computed 650: the sum ΣSp of the equivalent areas SP1 to SPn between the image points and their polynomial over the entire image, and a normalized sum NΣSp of said distances by means of division of the sum ΣSp by the total length LT of the lines found in the image.

This number represents an overall extent of the deformations in the region of the line edges.

To obtain a value that is reproducible from one examination to the next, the method comprises computing 660 an overall score consisting of the sum A of the normalized sums NΣSp over a series of images from the start time t0 to a given time t.

Figure 16:
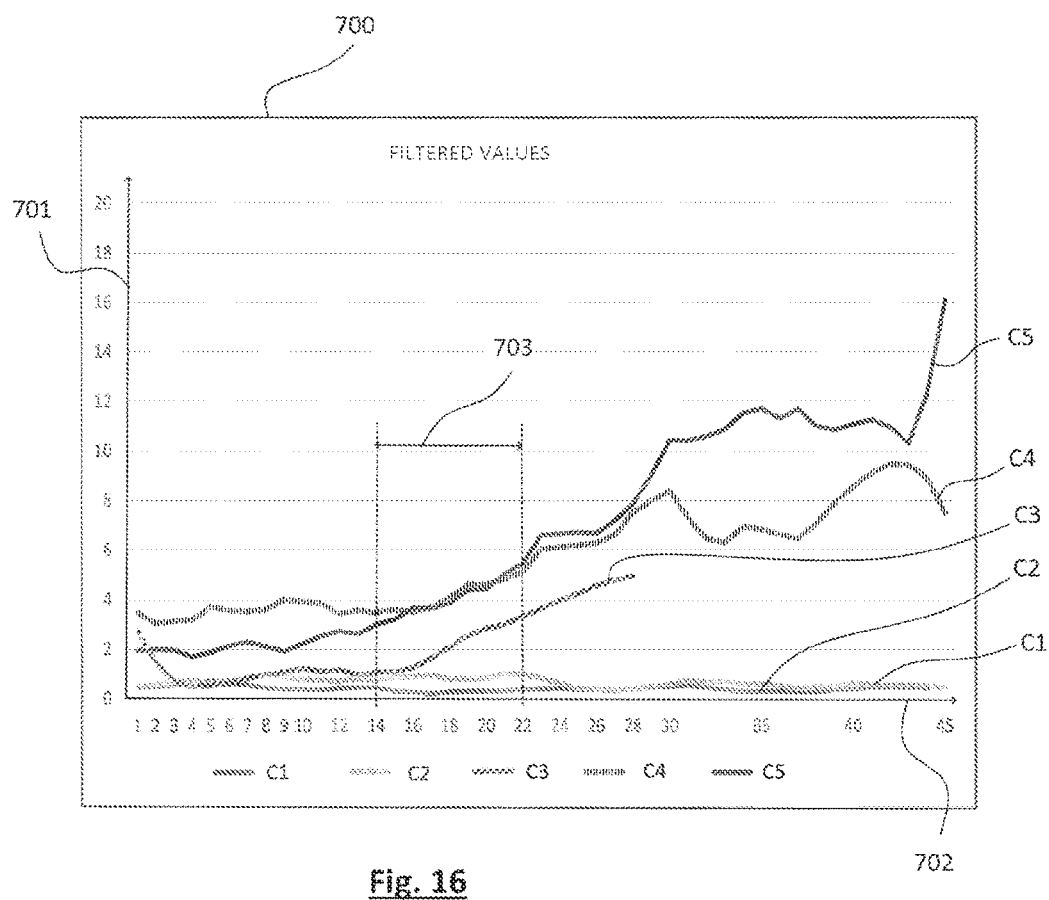
FIG. 16 shows a first graph of smoothed curves for a plurality of patients.
Figure 17:
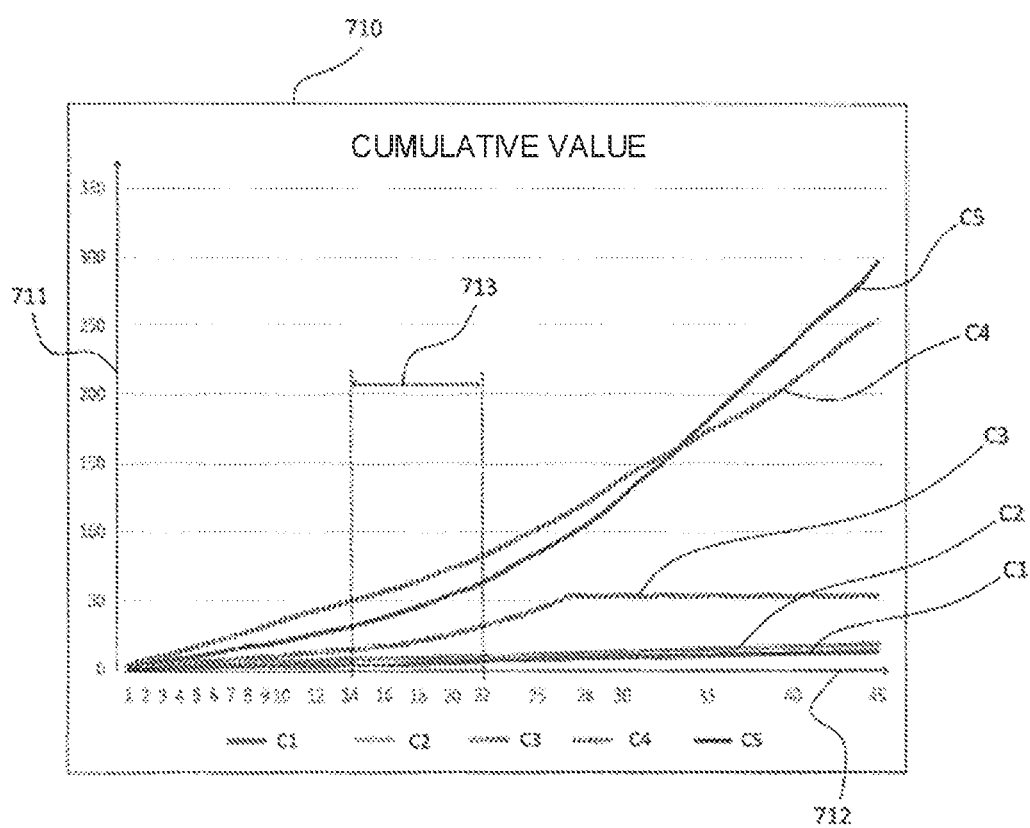
FIG. 17 shows a second graph of curves of cumulative values for a plurality of patients.

In the examples of curves in FIGS. 16 and 17, it may be seen that a sum over a time of the order of 6 seconds, i.e. 18 images when the images are taken every 0.3 seconds, allows differences between patients to be discerned.

The method may further comprise generating 550 a map of the locations of the micro-movements image by image, this allowing more marked regions of instability in the tear film to be identified and the variation in the deformations of the film over time to be observed.

It is also possible to compute and store the time of appearance of the points of micro-movement of the tear film and/or the rate of appearance of points of micro-movement of the tear film 560, this possibly aiding comparison of results during a treatment.

Furthermore, all or some of the computed data may be stored with a view to monitoring the patient and comparing said data over a plurality of examinations.

Once measurement is over, the practitioner will have at his disposal, on the one hand, a spatial and temporal map of the micro-movements of the tear film on the corneal surface and, on the other hand, a time-dependent curve tracing the variation in these micro-movements of the tear film as a function of time. The amplitude at each point of the curve will reveal the level of stability at a given time. The slope of this time-dependent curve will reveal the rate of appearance of break-ups in the tear film. This allows the interpretation of the examination performed to be refined.

FIG. 16 shows a graph 700 in which the y-axis 701 represents normalized sums NΣSp filtered with a moving average over three images and the x-axis 702 represents the images for five patients C1 to C5.

Patients C1 and C2 exhibit few micro-movements, i.e. a low instability in their tear film as a function of time, patient C3 exhibits a moderate instability but did not keep his eye open throughout the whole sequence, and patients C4 and C5 exhibit high instability representative of dry eye.

FIG. 17 shows a graph 710 in which the y-axis 711 represents the cumulative value A of the successive images and the x-axis 702 represents the images. This graph amplifies the visibility of the growth of the regions of micro-movement for patients C4 and C5 with dry eye disease whereas patients C1 and C2 exhibit very little progression and patient C3 exhibits a moderate progression up to the blink at image 28.

In both graphs, temporal regions 703, 713 of about two seconds centered on the 18$^{th}$ image, i.e. in the present case 6 seconds after blinking, have been shown. It may be seen in the curves that this examination time, of about 6 seconds, alone is enough to allow results to be standardized and patients without dry eye problems to be distinguished from those who are afflicted thereby, without running the risk of the examination time being so long as to possibly occasion untimely blinking.

The present disclosure is not limited to the examples described above, merely by way of example, but encompasses any variant, such as any other distribution or variation in the height of the lines that those skilled in the art are able to envision, within the scope of the claimed protection. In particular, as stated above, the lines of the pattern, which are parallel horizontal lines in the shown example, may be replaced by parallel vertical lines, a rotation of the image for example allowing the image-processing means for detecting the deformations of the lines to be applied to this configuration without changing the direction thereof.

What is claimed is:

1. A method for measuring the stability of a tear film of a patient by means of a device comprising a backlit translucent plate equipped with a test chart that is positioned in front of at least one eye of a patient, and at least one digital photographic camera connected to a computing system provided with means for processing and analyzing images, an objective of the camera pointing toward the eye of the patient in order to photograph a reflection of the pattern of the test chart from the eye of the patient, characterized in that, the test chart being provided with a pattern consisting of a succession of alternating light and dark lines that reflect from the eye of the patient and the means for processing and analyzing images being configured to detect deformations of said light or dark lines of the pattern of the test chart reflected from the eye of the patient and to identify, via a comparison of the position of image points on the edge of the lines with respect to an estimated line edge of the lines, tear-film micro-movements revealed by these deformations, the method comprises, from a start time at which an eyelid blinks:

successively capturing images,
successively detecting regions of micro-movement in the images and successively computing and storing (520) data on the positions, area and number of regions of micro-movement of the tear film in each image by means of the means for processing and analyzing images, and
computing and storing, on the basis of the successively computed positions, area and number of regions of micro-movement of the tear film, a measurement of the amplitude of the regions of micro-movement as a function of time.

2. The method for measuring the stability of a tear film as claimed in claim 1, comprising capturing an image every 0.1 to 0.5 seconds.

3. The method for measuring the stability of a tear film as claimed in claim 1, wherein the step of successively capturing images ends with the first occurrence of one of the following events: end of a time delay or detection of a next eyelid blink.

4. The method for measuring the stability of a tear film as claimed in claim 1, comprising tracking the eye of the patient or eyes by means of an iris-tracking method, so as to reposition the regions of deformation of the tear film that are detected and stored with respect to the analyzed eye.

5. The method for measuring the stability of a tear film as claimed in claim 1, wherein the estimated line edges are computed by polynomial regression.

6. The method for measuring the stability of a tear film as claimed in claim 5, comprising determining a population of points representative of the regions of micro-movement observed in the image of the lines by computing, along the lines, the absolute value of the distance to the polynomial along the axis perpendicular to the general direction of the lines of pixels P1 to Pn of line edges of the image that are separated from the polynomial by a distance dP in pixels larger than a threshold, and storing, for the representative points P1 to Pn, the distances dP1 to dPn.

7. The method for measuring the stability of a tear film as claimed in claim 6, comprising, for each image, for said population of representative points, computing, for each pixel P1 to Pn, the equivalent area Sp=dP×pixel width×pixel height, and computing the sum ΣSp of the equivalent areas SP1 to SPn from the image points to their polynomial over the entire image and a normalized sum NΣSp of said distances by means of division of the sum ΣSp by the total length LT of the lines found in the image.

8. The method for measuring the stability of a tear film as claimed in claim 7, comprising computing an overall score consisting of the sum A of the normalized sums NΣSp over a series of images from the start time t0 to a given time t.

9. The method for measuring the stability of a tear film as claimed in claim 1, comprising generating a map of the locations of the micro-movements image by image.

10. The method for measuring the stability of a tear film as claimed in claim 1, comprising computing and storing the time of appearance of the points of micro-movement of a tear film and/or the rate of appearance of points of micro-movement of the tear film.

11. The method for measuring the stability of a tear film as claimed in claim 1, comprising storing, in a database, all or some of the computed data with a view to monitoring the patient and comparing said data over a plurality of examinations.

12. A computer program comprising instructions for implementing the method as claimed in claim 1 when this program is executed by a processor.

13. A computer-readable non-volatile storage medium on which is stored a program for implementing the method as claimed in claim 1 when this program is executed by a processor.

* * * * *